United States Patent [19]

Morinaga et al.

[11] 3,943,038

[45] Mar. 9, 1976

[54] METHOD FOR PRODUCING AMINO ACIDS BY CULTURING HYDROGEN-OXIDIZING BACTERIA

[75] Inventors: Yasushi Morinaga, Yokohama; Ayaaki Ishizaki, Kawasaki; Shin-ichiro Otsuka, Yokohama, all of Japan

[73] Assignee: Ajinomoto Co., Inc., Tokyo, Japan

[22] Filed: Aug. 13, 1974

[21] Appl. No.: 497,031

[30] Foreign Application Priority Data

Aug. 16, 1973 Japan.............................. 48-91953

[52] U.S. Cl.............. 195/28 R; 195/29; 195/31 F; 195/34; 195/47; 195/50
[51] Int. Cl.².......................................... C12D 13/06
[58] Field of Search......... 195/29, 28 R, 30, 47, 96, 195/50

[56] References Cited

UNITED STATES PATENTS 3,562,110 2/1971 Douros, Jr. et al.................. 195/28

*Primary Examiner*—A. Louis Monacell
*Assistant Examiner*—Robert J. Warden
*Attorney, Agent, or Firm*—Cooper, Dunham, Clark, Griffin & Moran

[57] ABSTRACT

Amino acids are produced by culturing hydrogen-oxidizing bacteria of the genus Arthrobacter, Brevibacterium and Mycobacterium in an aqueous culture medium in the presence of oxygen, hydrogen and carbon dioxide.

9 Claims, No Drawings

METHOD FOR PRODUCING AMINO ACIDS BY CULTURING HYDROGEN-OXIDIZING BACTERIA

This invention relates to a method for producing amino acids by culturing hydrogen oxidizing bacteria.

The cost of amino acids produced by fermentation depends largely on the cost of the carbon source used. In this respect, carbon dioxide is available at a low cost. Various autotrophic microorganisms are known to assimilate carbon dioxide, but none of them produces any amino acids from the assimilated carbon dioxide.

It has now been found that newly-discovered gram positive hydrogen-oxidizing bacteria, especially bacteria belonging to Arthrobacter, Brevibacterium and Micobacterium, can produce a number of amino acids from carbon dioxide as the carbon source and hydrogen as the energy source. It is further found that amino acid production is remarkably improved by adding penicillin to the culture medium. Amino acids produced in accordance with this invention include lysine, histidine, arginine, aspartic acid, threonine, serine, glutamic acid, proline, glycine, alanine, cysteine, valine, isoleucine, leucine, tyrosine, phenylalanine and methionine.

The bacteria useful in the practices of this invention have the following taxonomic characteristics:

Brevibacterium sp. AJ 3588 (FERM P 2234)

Morphology (cultivated autotrophically on inorganic agar medium for 42 hrs): Unicellular, non-spore-forming, small short rod, size 0.5 × 0.5–1.5 $\mu$, motile by means of lateral flagella, gram positive, not acid-fast, the arrangement of cells is very unique. Cells are arranged side by side like cartridge belt.

Agar colony type: (cultivated autotrophically for 10 days on inorganic agar plate); 6.0 mm in diameter, rosulate, rugose, flat, filamentous, yellowish gray, transparent. (cultivated heterotrophically for 5 days on yeast malt agar plate); 7.0 mm in diameter, circular, smooth, umbonate, ciliate, yellowish gray, opaque.

Hydrolysis of gelatin: positive.
BCP milk: alkalinized and completely peptonized.
Production of $H_2S$: positive.
Production of nitrite from nitrate: positive.
Methyl red test: negative.
Production of acetyl-methyl-carbinol: negative.
Production of indole: negative.
Utilization of citrate: not utilized.
Hydrolysis of starch: negative.
Catalase test: positive.
Oxidase test: positive.
Optimum growth temperature: 25° – 30°C.
Optimum pH: pH 5.5 – 7.5.

Acid production from carbohydrates: (Hugh and Leifson's method); acid produced aerobically from glycerol, acid not produced from glucose, lactose, D-arabinose, D-xylose, D-mannose and maltose.

Utilization of organic compounds as a sole carbon source: ethanol, glycerol, glucose, fructose, sucrose, trehalose, succinate, gluconate, acetate, para-hydroxybenzoate, metahydroxybenzoate and normal alkanes ($C_8$ – $C_{18}$) are utilized. Methanol, lactose, D-arabinose, D-xylose, D-mannose, maltose, D-galactose, D-ribose, malonate, oxalate, formate, phenol, methane and butane are not utilized.

Guanine and cytosine content of DNA (GC-content): 67.8%.

This strain is identified as a species of the genus Brevibacterium, since this strain is a gram positive, short rod, non-spore-forming, not acid fast and does not exhibit plemorphism. There are four species of Brevibacterium described in the Bergey's Manual of Determinative Bacteriology, 7th edition, which have motility and ability to hydrolyze gelatin. Among them, this organism resembles B. lipolyticum by colony type, but it is different from B. lipolyticum, for instance, in flagellation, production of $H_2S$, nitrate reduction, and optimum growth temperature. We consider it correct to identify this organism as a new species of Brevibacterium, because it can grow autotrophically and has a unique cell arrangement.

Mycobacterium sp. AJ 3589 (FERM P 2235)

Morphology (cultivated autotrophically on inorganic agar medium for 42 hrs): unicellular, non-spore-forming, unbranched, rod shaped, 0.5 × 1.0–1.5 $\mu$, non-motile, gram positive, acid fast (14 – 20 hrs culture), cells become oval and gram negative in older culture.

Agar colony type: (cultivated autotrophically for 10 days on inorganic agar plate); 1.5 mm in diameter, circular, flat, rough, deutate, pale yellow or colorless, opaque. (cultivated heterotrophically for 6 days on yeast malt agar plate); 3.0 mm in diameter, circular, striate, umbonate, entire, grayish white, opaque.

Hydrolysis of gelatin: negative.
BCP milk: strongly alkalinized and slowly digested.
Production of $H_2S$: positive.
Production of nitrite from nitrate: weakly positive.
Methyl red test: negative.
Production of acetyl-methyl-carbinol: negative.
Production of indole: negative.
Utilization of citrate: negative.
Hydrolysis of starch: negative.
Catalase test: positive.
Oxidase test: negative.
Optimum temperature: 25° – 30°C.
Optimum pH: pH 6.0 – 8.0.

Acid production from carbohydrates: (Hugh and Leifson's method): acid produced aerobically from glycerol, acid not produced from glucose, lactose, D-arabinose, D-xylose, D-mannose, and maltose.

Utilization of organic compounds as a sole carbon source: ethanol, glycerol, glucose, fructose, D-mannose, D-galactose, D-ribose, trehalose, succinate, gluconate, acetate and normal alkanes ($C_{11}$–$C_{18}$) are utilized. Methanol, lactose, D-arabinose, D-xylose, sucrose, maltose, malonate, oxalate, formate, parahydroxybenzoate, meta-hydroxybenzoate, phenol and normal alkanes ($C_1$–$C_{10}$) are not utilized.

It is clear that this organism belongs to the genus Mycobacterium, since this organism is non-spore-forming, gram positive, rod, acid fast and non-motile. This organism resembles *Mycobacterium fortuitum* as to the colony type, but it is different from *M. fortuitum* in starch hydrolyzation, acid production from glucose and mannose, growth temperature, acid fastness on early stage of growth and ability to grow autotrophically. For this reason, this organism is identified as a new species of Mycobacterium.

Arthrobacter sp. AJ 3786 (FERM P 2638)

Morphology (cultivated autotrophically on inorganic agar medium for 42 hrs): non-spore-forming, rod-shaped, cells are remarkably irregular, size 0.8 × 1.5–4.0 $\mu$, non-motile, gram positive in young culture but negative in aged culture, not acid fast. In aged cultures, cells become coccoidal. Cystites are not formed. It does not exhibit a definite cycle of development.

Agar colony type: (cultivated autrotrophically for 10 days on inorganic agar plate); 2.5 mm in diameter, circular, convex, smooth, entire, light reddish yellow, (fringe of colonies are pale yellow), opaque. (cultivated heterotrophically for 5 days on yeast malt agar plate): 4.0 mm in diameter, circular, smooth, raised, entire, light reddish yellow, (fringe of colonies are pale yellow), opaque.

Hydrolysis of gelatin: negative.
BCP milk: slowly alkalinized.
Production of $H_2S$: negative.
Production of nitrite from nitrate: positive.
Methyl red test: negative.
Production of acetylmethyl carbinol: negative.
Production of indole: negative.
Utilization of citrate: negative.
Hydrolysis of starch: negative.
Catalase test: positive.
Oxidase test: negative.
Optimum growth temperature: 28° – 30°C.
Optimum pH: pH 5.5 – 7.5.

Acid production from carbohydrates (Hugh and Leifson's method): acid not produced from glucose, lactose, D-arabinose, D-xylose, D-mannose, maltose and glycerol.

Utilization of organic compounds as a sole carbon source: ethanol, glucose, fructose, sucrose, citrate, succinate, gluconate are utilized, methanol, lactose, D-arabinose, D-xylose, D-mannose, maltose, D-galactose, D-ribose, trehalose, acetate, malonate, oxalate, formate, para-hydroxybenzoate, meta-hydroxybenzoate, phenol and normal alkanes are not utilized.

Guanine and cytosine content of DNA (GC-content): 64.4%.

On the basis of morphological observations, this organism should be a coryne-form bacteria, because of irregularity of cell shapes, tendency to become coccoidal cells in aged cultures and indistinctness of grams reaction. Among coryne-form bacteria, this organism seems to be belonging to the genus Corynebacterium or Arthrobacter because of irregularity of cell shapes.

This organism AJ 3786 should be assigned to the genus Arthrobacter, because the diphtherial type bacteria are typical species of the genus Corynebacterium, and the characteristics of AJ 3786 are basically different from diphtherial type bacteria. There is no known species of the genus Arthrobacter which this strain can be identified with and, accordingly, it is believed this is a new species of Arthrobacter since none of the known species of Arthrobacter can grow autothropically.

Aqueous culture media for culturing the microorganisms of this invention contain nitrogen sources and inorganic salts. Suitable nitrogen sources include ammonium salts, aqueous ammonia, gaseous ammonia, and nitrate salts. Inorganic salts useful in the media are the conventional salts of potassium, sodium, the phosphate salts, the calcium salts, the sulfate salts, the ferrous salts, the manganese salts, the zinc salts and others.

Sometimes microbial growth is promoted by the addition of small amounts of organic nutrients such as amino acids or vitamins, and small amounts of materials containing those organic nutrients, such as yeast extract, bouillon, corn steep liquor, casein hydrolyzate, malt extract, soy protein or its hydrolyzate.

The addition of penicillin, such as benzylpenicillin, phenoxymethylpenicillin, or ampicillin, to the culture medium usually improves the production of amino acids. Preferably 5 to 100 IU/ml penicillin are added during 50 to 80 hours cultivation.

During the cultivation, hydrogen, oxygen and carbon dioxide are maintained in or supplied to the fermentation vessel containing the culture medium. The gases are introduced into the fermentation vessel preferably in the ratio of 10 to 80% by volume hydrogen, 5 to 25% by volume oxygen and 3 to 20% by volume carbon dioxide.

Culturing is carried out desirably at 20 to 35°C and pH 4 to 9 for 1 to 7 days. pH is maintained by supplying gaseous ammonia which also suitably serves as a nitrogen source.

Amino acids accumulated in the culture broth are recovered by any known method. For example, after removing the cells by centrifuging and evaporating the supernatant, amino acids are precipitated by adjusting the pH to isoelectric point, or the amino acids may be separated by using ion exchange resin.

EXAMPLE 1

An aqueous culture medium was prepared containing, per deciliter, 0.5 g $(NH_4)_2SO_4$, 0.03 g $KH_2PO_4$, 0.18 g $Na_2HPO_4.12 H_2O$, 0.02% $MgSO_4.7H_2O$, 100 mg $FeSO_4.7H_2O$, 100 mg $CaCl_2.2H_2O$, and adjusted to a pH 7.2. 400 ml. batches of the medium were placed in 1 liter-fermentation vessel and sterilized with steam. Each batch of medium was inoculated with one of gram positive hydrogen-oxidizing bacteria, i.e., Brevibacterium sp. AJ 3588, Mycobacterium sp. AJ 3589 and Arthrobacter sp. AJ 3786, or one of gram negative hydrogen-oxidizing bacteria, i.e., Alcaligenes eutrophus ATCC 17697, Pseudomonas facilis ATCC 11228, and Pseudomonas ruhlandii ATCC 15749, and held at 30°C with agitating at 1200 r.p.m.

During the cultivation, hydrogen, carbon dioxide and air were introduced at the rate of 18 ml/min., 5 ml/min. and 22 ml/min. respectively. The pH of the medium was maintained at 6.8 with gaseous ammonia.

After 96 hours cultivation or culturing, the amino acids produced in the culture broth were determined by an amino acid autoanalyzer. The results are shown in Table 1.

Table 1

| amino acid mg/dl | gram positive bacteria | | | gram negative bacteria | | |
|---|---|---|---|---|---|---|
| | Brevibacterium sp. Ferm P-2234 | Mycobacterium sp. Ferm P-2235 | Arthrobacter sp. Ferm P-2638 | Alcaligenes eutrophus ATCC 17697 | Pseudomonas facilis ATCC 11228 | Pseudomonas ruhlaudii ATCC 15749 |
| lysine | 0.86 | 0.54 | 0.72 | 0.03 | 0.02 | 0.02 |
| histidine | 0.45 | 0.31 | 0.40 | 0.02 | 0.02 | 0.03 |
| arginine | 1.45 | 0.98 | 1.33 | 0.08 | 0.04 | 0.03 |
| aspartic acid | 9.48 | 8.25 | 6.24 | 0.13 | 0.09 | 0.18 |

Table 1-continued

| amino acid mg/dl | gram positive bacteria | | | gram negative bacteria | | |
|---|---|---|---|---|---|---|
| | Brevibacterium sp. Ferm P-2234 | Mycobacterium sp. Ferm P-2235 | Arthrobacter sp. Ferm P-2638 | Alcaligenes eutrophus ATCC 17697 | Pseudomonas facilis ATCC 11228 | Pseudomonas ruhlaudii ATCC 15749 |
| threonine | 5.10 | 2.60 | 1.52 | 0.06 | 0.03 | 0.02 |
| serine | 2.23 | 1.97 | 1.04 | 0.02 | 0.02 | 0.04 |
| glutamic acid | 25.46 | 18.41 | 14.37 | 0.45 | 0.42 | 0.69 |
| proline | 3.87 | 2.33 | 1.04 | 0.03 | 0.04 | 0.03 |
| glycine | 5.06 | 2.48 | 1.80 | 0.05 | 0.05 | 0.08 |
| alanine | 12.77 | 8.50 | 3.20 | 0.04 | 0.08 | 0.09 |
| cysteine | 0.48 | 0.37 | 0.22 | 0.01 | 0.01 | 0.01 |
| valine | 4.39 | 13.29 | 3.01 | 0.05 | 0.06 | 0.04 |
| isoleucine | 1.89 | 1.47 | 0.89 | 0.02 | 0.02 | 0.02 |
| leucine | 3.96 | 6.61 | 1.20 | 0.03 | 0.04 | 0.04 |
| tyrosine | 1.97 | 0.32 | 0.33 | 0.02 | 0.01 | 0.02 |
| phenylalanine | 2.50 | 1.57 | 0.85 | 0.02 | 0.02 | 0.02 |
| methionine | 1.15 | 0.80 | 0.40 | 0.01 | 0.01 | 0.01 |

EXAMPLE 2

The hydrogen-oxidizing bacteria of Example 1 were cultured in the same manner as described in Example 1.

Penicillin G (50 IU/ml) was added to the media of Brevibacterium sp. AJ 3588 and Mycobacterium sp. AJ 3589 after 68 hours cultivation and to the media of Arthrobacter sp. AJ 3786, Alealigenes eutrophus ATCC 17697, Pseudomonas facilis ATCC 11228, and Pseudomonas ruhlandii ATCC 15749 after 48 hours.

Aspartic acid and glutamic acid accumulated in the culture broth are shown in Table 2.

Table 2

| | Brevibacterium sp. Ferm P-2234 | Mycobacterium sp. Ferm P-2235 | Arthrobacter sp. Ferm P-2638 | Alcaligenes eutrophus ATCC 17697 | Pseudomonas facilis ATCC 11228 | Pseudomonas ruhlandii ATCC 15749 |
|---|---|---|---|---|---|---|
| aspartic acid mg/dl | 27.60 | 24.37 | 19.70 | 0.14 | 0.12 | 0.29 |
| glutamic acid mg/dl | 205.8 | 179.5 | 159.4 | 0.50 | 0.58 | 0.88 |

Microorganisms identified by FERM P numbers and ATCC numbers have been deposited in, and are available to qualified persons without permission from the Fermentation Research Institute, Agency of Industrial Science and Technology, at 1-8-5, Inage-higashi, Chiba-shi, Chiba, Japan, and American Type Culture Collection, at 12301 Parklawn Drive, Rockville, Md. 20852.

What is claimed is:

1. A method for producing amino acids which comprises culturing a microorganism selected from the group consisting of brevibacterium sp. FERM P-2234, mycobacterium sp. FERM P-2235, arthrobacter sp. FERM P-2638, alcaligenes eutrophus ATCC 17697, pseudomonas facilis ATCC 11228 and pseudomonas ruhlaudii ATCC 15749 in an aqueous culture medium containing at least a nitrogen source and inorganic salt and in the presence of oxygen, hydrogen and carbon dioxide, and recovering the resulting produced amino acids from the culture medium.

2. A method as set forth in claim 1, wherein said microorganism is Arthrobacter sp. FERM P 2638.

3. A method as set forth in claim 1, wherein said microorganism is Brevibacterium sp. FERM P 2234.

4. A method as set forth in claim 1, wherein said microorganism is Mycobacterium sp. FERM P 2235.

5. A method as set forth in claim 1, wherein said amino acids include lysine, histidine, arginine, aspartic acid, threonine, serine, glutamic acid, proline, glycine, alanine, cysteine, valine, isoleucine, leucine, tyrosine, phenylalanine, or methionine.

6. A method as set forth in claim 1, wherein said culture medium contains penicillin.

7. A method as set forth in claim 1 wherein said microorganism is alcaligenes eutrophus ATCC 17697.

8. A method as set forth in claim 1 wherein said microorganism is pseudomonas facilis ATCC 11228.

9. A method as set forth in claim 1 wherein said microorganism is pseudomonas ruhlaudii ATCC 15749.

* * * * *